United States Patent
Geddes

(10) Patent No.: US 11,435,343 B2
(45) Date of Patent: *Sep. 6, 2022

(54) METAL-ENHANCED BIOLUMINESCENCE: AN APPROACH FOR MONITORING BIOLOGICAL BIOLUMINESCENT PROCESSES

(71) Applicant: UNIVERSITY OF MARYLAND, BALTIMORE COUNTY, Baltimore, MD (US)

(72) Inventor: Chris D. Geddes, Bel-Air, MD (US)

(73) Assignee: UNIVERSITY OF MARYLAND, BALTIMORE COUNTY, Baltimore, MD (US)

(*) Notice: Subject to any disclaimer, the term of this patent is extended or adjusted under 35 U.S.C. 154(b) by 635 days.

This patent is subject to a terminal disclaimer.

(21) Appl. No.: 16/028,950

(22) Filed: Jul. 6, 2018

(65) Prior Publication Data

US 2018/0321232 A1    Nov. 8, 2018

Related U.S. Application Data

(62) Division of application No. 13/201,878, filed as application No. PCT/US2010/024367 on Feb. 17, 2010, now Pat. No. 10,024,850.

(Continued)

(51) Int. Cl.
- *G01N 33/543* (2006.01)
- *G01N 21/76* (2006.01)
- *G01N 21/64* (2006.01)

(52) U.S. Cl.
CPC ..... *G01N 33/54373* (2013.01); *G01N 21/763* (2013.01); *G01N 21/648* (2013.01)

(58) Field of Classification Search
CPC .......... G01N 33/54373; G01N 21/763; G01N 21/648

(Continued)

(56) References Cited

U.S. PATENT DOCUMENTS

| 5,017,009 A | 5/1991 | Schutt et al. |
| 5,449,918 A | 9/1995 | Krull et al. |

(Continued)

FOREIGN PATENT DOCUMENTS

| WO | 198909408 | 10/1989 |
| WO | 2004024191 | 3/2004 |

(Continued)

OTHER PUBLICATIONS

K. Aslan, Z. Leonenko, J. R. Lakowicz, and C. D. Geddes, Annealed silver-island films for applications in metal-enhanced fluorescence: Interpretation in terms of radiating plasmons, J Fluoresc 15,643-654 (2005).

(Continued)

*Primary Examiner* — Christopher L Chin

(74) *Attorney, Agent, or Firm* — Tristan A. Fuierer; Casimir Jones, S.C.

(57) ABSTRACT

The present invention relates to surface plasmon-coupled bioluminescence, wherein bioluminescent emission from a bioluminescent chemical reaction couples to surface plasmons in metalized particles thereby enhancing the signal. Importantly, these plasmonic emissions emitted from metallic particles generated without an external excitation source but instead from induced electronically excited states caused by the bioluminescent chemical reaction.

12 Claims, 4 Drawing Sheets

Related U.S. Application Data

(60) Provisional application No. 61/153,270, filed on Feb. 17, 2009.

(58) Field of Classification Search
USPC ....... 422/82.05; 435/8, 288.7, 808; 436/525, 436/527, 530, 164, 172, 805
See application file for complete search history.

(56) References Cited

U.S. PATENT DOCUMENTS

| | | | |
|---|---|---|---|
| 5,866,433 | A | 2/1999 | Schalkhammer et al. |
| 7,095,502 | B2 | 8/2006 | Lakowicz et al. |
| 7,253,452 | B2 | 8/2007 | Steckel et al. |
| 7,348,182 | B2 | 3/2008 | Martin et al. |
| 7,351,590 | B2 | 4/2008 | Martin |
| 7,400,397 | B2 | 7/2008 | Lakowicz et al. |
| 7,648,834 | B2 | 1/2010 | Moore |
| 7,718,445 | B2 | 5/2010 | Martin |
| 7,718,804 | B2 | 5/2010 | Geddes et al. |
| 7,732,215 | B2 | 6/2010 | Geddes et al. |
| 7,939,333 | B2 | 5/2011 | Geddes et al. |
| 8,008,067 | B2 | 8/2011 | Geddes et al. |
| 8,034,633 | B2 | 10/2011 | Geddes |
| 8,075,956 | B2 | 12/2011 | Geddes et al. |
| 9,459,212 | B2 * | 10/2016 | Geddes ............... G01N 33/553 |
| 10,024,850 | B2 | 7/2018 | Geddes |
| 2003/0108980 | A1 | 6/2003 | Sayler et al. |
| 2003/0228682 | A1 | 12/2003 | Lakowicz et al. |
| 2004/0063165 | A1 | 4/2004 | Gawad |
| 2004/0157237 | A1 | 8/2004 | Malak et al. |
| 2004/0197793 | A1 * | 10/2004 | Hassibi ............... C12Q 1/6825 435/6.12 |
| 2005/0053974 | A1 | 3/2005 | Lakowicz et al. |
| 2005/0123563 | A1 * | 6/2005 | Doranz ............... A61K 47/6901 424/204.1 |
| 2006/0147927 | A1 | 7/2006 | Geddes et al. |
| 2007/0269826 | A1 | 11/2007 | Geddes et al. |
| 2008/0160637 | A1 * | 7/2008 | Kang ............... B82Y 30/00 436/524 |
| 2008/0215122 | A1 | 9/2008 | Geddes et al. |
| 2009/0022766 | A1 | 1/2009 | Geddes et al. |
| 2009/0325199 | A1 | 12/2009 | Geddes et al. |
| 2010/0028983 | A1 * | 2/2010 | Geddes ............ G01N 33/54393 435/287.2 |
| 2010/0062545 | A1 | 3/2010 | Geddes et al. |
| 2010/0209937 | A1 | 8/2010 | Geddes et al. |
| 2010/0297016 | A1 | 11/2010 | Geddes et al. |
| 2011/0020946 | A1 | 1/2011 | Geddes |
| 2011/0207236 | A1 | 8/2011 | Geddes |
| 2012/0282630 | A1 | 11/2012 | Geddes |

FOREIGN PATENT DOCUMENTS

| | | |
|---|---|---|
| WO | 2006074130 | 7/2006 |
| WO | 2010033677 | 3/2010 |

OTHER PUBLICATIONS

K. Aslan, J. R. Lakowicz, and C. D. Geddes, Nanogold plasmon resonance-based glucose sensing. 2. Wavelength-ratiometric resonance light scattering, Analytical Chemistry 77, 2007-2014 (2005).
K. Aslan, I. Gryczynski, J. Malicka, E. Matveeva, J. R. Lakowicz, and C. D. Geddes, Metal-enhanced fluorescence: an emerging tool in biotechnology, Curr Opin Biotechnol 16,55-62 (2005).
K. Aslan, M. Wu, J. R. Lakowicz, and C. D. Geddes, Fluorescent core-shell Ag@SiO2 nanocomposites for metal-enhanced fluorescence and single nanoparticle sensing platforms, J Am Chem Soc 129,1524-1525 (2007).
K. Aslan, S. N. Malyn, and C. D. Geddes, Angular-dependent metal-enhanced fluorescence from silver colloid-deposited films: opportunity for angular-ratiometric surface assays, Analyst 132,1112-1121 (2007).
K. Aslan and C. D. Geddes, New tools for rapid clinical and bioagent diagnostics: microwaves and plasmonic nanostructures , Analyst 133,1469-1480 (2008).
K. Aslan and C.D. Geddes, A review of an ultrafast and sensitive bioassay platform technology: Microwave-accelerated metal-enhanced fluorescence , Plasmonics 3,89-101 (2008).
K. Aslan, S. N. Malyn, and C. D. Geddes, Angular-dependent metal-enhanced fluorescence from silver island films, Chem Phys Lett 453,222-228 (2008).
K. Aslan, M. J. Previte, Y. Zhang, T. Gallagher, L. Baillie, and C. D. Geddes, Extraction and detection of DNA from *Bacillus anthracis* spores and the vegetative cells within 1 min , Anal Chem 80,4125-4132 (2008).
S. Belkin, D. R. Smulski, A. C. Vollmer, T. K. Van Dyk, and R. A. LaRossa, Oxidative stress detection with *Escherichia coli* harboring a katG'::lux fusion , Appl Environ Microbiol 62,2252-2256 (1996).
Chowdhury, M.H. et al., Metal-Enhanced Chemiluminescen, J. Fluoresc. vol. 16, pp. 295-299, May 12, 2006.
M.H Chowdhury, K. Aslan, S.N. Malyn, J.R. Lakowicz, and C.D. Geddes, Metal-enhanced chemiluminescence: Radiating plasmons generated from chemically induced electronic excited states, Applied Physics Letters 88, 173104-1-3 (2006).
E. Eltzov, D. Zeevi, A. Kushmaro, and R. S. Marks, Detection of sub-inhibitory antibiotic concentrations via luminescent sensing bacteria and prediction of their mode of action, Sensors and Actuators B: Chemical 129,685-692 (2008).
T. Fine, P. Leskinen, T. Isobe, H. Shiraishi, M. Morita, R. S. Marks, and M. Virta, Luminescent yeast cells entrapped in hydrogels for estrogenic endocrine disrupting chemical biodetection , Biosensors & Bioelectronics 21,2263-2269 (2006).
J. R. Lakowicz, C. D. Geddes, I. Gryczynski, J. Malicka, Z. Gryczynski, K. Aslan, J. Lukomska, E. Matveeva, J. Zhang, R. Badugu, and J. Huang, : Advances in surface-enhanced fluorescence , J Fluoresc 14,425-441 (2004).
S. Link and M.A. El-Sayed, Spectral properties and relaxation dynamics of surface plasmon electronic oscillations in gold and silver nanodots and nanorods, The Journal of Physical Chemistry B 103,8410-8426 (1999).
E. A. Meighen, Bacterial Bioluminescence—Organization, Regulation, and Application of the Lux Genes, Faseb J 7,1016-1022 (1993).
S. K. Nordeen, Luciferase Reporter Gene Vectors for Analysis of Promoters and Enhancers, Biotechniques 6,454-458 (1988).
R. Pedahzur, B. Polyak, R. S. Marks, and S. Belkin, Water toxicity detection by a panel of stress-responsive luminescent bacteria , J Appl Toxicol 24,343-348 (2004).
B. Polyak, S. Geresh, and R. S. Marks, Synthesis and characterization of a biotin-alginate conjugate and its application in a biosensor construction , Biomacromolecules 5,389-396 (2004).
B. Polyak, E. Bassis, A. Novodvorets, S. Belkin, and R. S. Marks, Optical fiber bioluminescent whole-cell microbial biosensors to genotoxicants, Wat Sci Technol 42,305-311 (2000).
P.J. Tarcha, J. DeSaja-Gonzalez, S. Rodriquez-Llorente, and R. Aroca, Surface-enhanced fluorescence on SiO2-coated silver island films, Applied Spectroscopy 53,43-48 (1999).
G. Bauer, F. Pittner and Th. Schalkhammer, Metal Nano-Cluster Biosensors, Mikrochim. Acta 131, 107-114 (1999).
Th. Schalkhammer, Metal Nano Clusters as Transducers for Bioaffinity Interactions, Monatschefte für Chemie 129, 1067-1092(1998).
T. Troy, D. Jekic-McMullen, L. Sambucetti, and B. Rice, Quantitative Comparison of the Sensititivity of Detection of Fluorescent and Bioluminescent Reporters in Animal Models, Mol Imaging 3,9-23 (2004).
A. Wokaun, H. P. Lutz, A.P. King, U.P. Wild, and R.R. Ernst, : Energy-Transfer in Surface Enhanced Luminescence , Journal of Chemical Physics 79,509-514 (1983).
Y. Zhang, K. Aslan, M. J. Previte, S. N. Malyn, and C. D., Metal-enhanced phosphorescence: Interpretation in terms of triplet-coupled radiating plasmons, Geddes, J Phys Chem B 110,25108-25114 (2006).
Y. Zhang, K. Aslan, S.N. Malyn, and C.D. Geddes, Metal-enhanced phosphorescence (MEP), Chemical Physics Letters 427 432-437 (2006).

(56) References Cited

OTHER PUBLICATIONS

Geddes and Lakowicz, eds Topics in Fluor Spect pub Springer, 2005, vol. 8, p. 405-448.
Troy (2004) Mol Imag 3:9-23.
Chowdhury (2006) Ap Phy Ltr 88: 173104-1-173104-3.
Giubellino (2007) Canc Res 67: 6012-6016.
Wikipedia entry for chemiluminescence.
Van Dyk, Tina K, et al.; "Rapid and sensitive pollutant detection by induction of heat shock gene-bioluminescence gene fusions," Applied and Environmental Microbiology, 1994, pp. 1414-1420, vol. 60.

* cited by examiner

METAL-ENHANCED BIOLUMINESCENCE: AN APPROACH FOR MONITORING BIOLOGICAL BIOLUMINESCENT PROCESSES

CROSS REFERENCE TO RELATED APPLICATIONS

The present application is a divisional application of co-pending U.S. patent application Ser. No. 13/201,878 filed on Sep. 26, 2011, now U.S. Pat. No. 10,024,850 issued on Jul. 17, 2018, which was filed under the provisions of 35 U.S.C § 371 and claims priority to International Patent Application No. PCT/US2010/024367 filed on 17 Feb. 2010, which claims priority to U.S. Provisional Patent Application No. 61/153,270 filed on Feb. 17, 2009 the contents of which are hereby incorporated by reference herein for all purposes.

BACKGROUND OF THE INVENTION

Field of the Invention

The present invention relates to enhancement of bioluminescence signatures of a chemical reaction in an organism or tissue by positioning the organism or tissue near metallic particles.

Background of the Related Art

Metal-Enhanced Fluorescence has been described in detail over the last 5 years as a technology for enhancing fluorescence[1-3], phosphorescence[4,5] and chemiluminescence[6] signatures by the close proximity of metallic nanostructures. In the near-field, i.e. at distances less than 100 Å from the surface, excited states can non-radiatively induce mirror dipoles in the metallic surface, the surface plasmons in turn, radiating the coupled quanta efficiently. Typically, one observes enhanced far-field radiation (lower detection limits when MEF is applied to Immunoassays[7,8]), with considerably shorter luminescent lifetimes, which are though to reflect the very short plasmon lifetimes themselves.[9] Since the lifetimes are considerably reduced, one often observes enhanced luminophore photostability, as the luminescent species spend less time in an excited state and are therefore less prone to destructive excited state process, such as photo-oxidation. Subsequently, MEF affords for ultra-bright and ultra-stable luminescence probes' and detection platforms[7,8,11] to be realized.

For both fluorescent and phosphorescent probes, which generically require an external light source for electronic excitation, an additional electric field effect also enhances the far-field luminescent yield by an increase in the absorption-cross section of the fluorophore in the coupled fluorophore-metal system. For systems where no external light source is used for excitation, such as for chemiluminescence, (chemically induced electronic excited states), dramatic MEF enhancements have also been reported, even in the absence of an electric field component, with 1000-fold increases in chemiluminescence reported.[6]

Traditionally, bioluminescence signatures are relatively weak as compared to fluorescence-based probes with sensitive detectors often employed.[12] Bioluminescence is found in microorganisms [i.e., some bacteria (mostly marine forms, e.g., *Vibrio fischeri*), fungi, and dinoflagellates], insects (e.g., the firefly, *Photinus pyradis*), some crustaceans (i.e., *Cypridine hilgendorfi*), jellyfish, worms and other invertebrates and even in mammals. Although the biochemical mechanism of luminescence is known to vary (i.e., the luminescence system found in bacteria is different from that found in fireflies and dinoflagellates), light production in living organisms is most frequently catalyzed by the enzyme luciferase. Bacterial luciferase is a mixed function oxidase, consisting of two different subunits each with a molecular weight of approximately 40,000 daltons.

Bioluminescence is used for quantitative determinations of specific substances in biology and medicine. For example, luciferase genes have been cloned and exploited as reporter genes in numerous assays, for many purposes. Since the different luciferase systems have different specific requirements, they may be used to detect and quantify a variety of substances. The majority of commercial bioluminescence applications are based on firefly [*Photinus pyralis*] luciferase.

One of the first and still widely used assays involves the use of firefly luciferase to detect the presence of ATP. It is also used to detect and quantify other substrates or co-factors in the reaction. Any reaction that produces or utilizes NAD(H), NADP(H) or long chain aldehyde, either directly or indirectly, can be coupled to the light-emitting reaction of bacterial luciferase. Another luciferase system that has been used commercially for analytical purposes is the Aequorin system. The purified jellyfish photoprotein, aequorin, is used to detect and quantify intracellular $Ca^{2}+$ and its changes under various experimental conditions.

These methods suggest activation of the reporter luciferase genes with emission of a readily detectable light signal which allows the monitoring of bacterial response in real-time, by simple luminometry (e.g. fiber optic, luminometers).[13,14] The most commonly used systems are the luc gene from the firefly and lux genes from bacterial species of the genus *Vibrio*. Expression of the lux luciferase operon produces light without any additions, allowing thereby on-line monitoring of gene expression; whereas the expression of firefly luciferase genes requires externally added substrate (luciferin) for luminescence. The bacterial lux system is expressed very effectively in different bacterial strains and this method has been widely applied for different applications.[15-17] These luciferases and related reagents are used as reagents for diagnostics, quality control, environmental testing and other such analyses.

However current testing methods are very slow with limited sensitivity and such shortcomings can be critical in regard to bacterial diseases of humans and animals. Thus it would be advantageous to develop a system and method to overcome the shortcomings of prior art testing methods.

SUMMARY OF THE INVENTION

The present invention relates to surface plasmon-coupled bioluminescence, wherein bioluminescent emission from a bioluminescent chemical reaction couples to surface plasmons in metalized particles thereby enhancing the signal. Importantly, these plasmonic emissions emitted from metallic particles are generated without an external excitation source but instead from induced electronically excited states caused by the oxidation of a luciferin by bioluminescent organisms or expression of the lux luciferase operon. Bioluminescent organisms may include bacteria, dinoflagellates, fungi, jellyfish, worms, insects, crustaceans, millipedes, squid, and fish.

In one aspect, the present invention relates to a system for measuring bioluminescence emissions, the system comprising:

a) a multiplicity of metallic containing particles attached to a substrate or free in solution and positioned at a distance from the bioluminescence based reactions to enhance emissions of such reactions; wherein bioluminescence based reactions causes emission of light and excitation of metallic surface plasmons, wherein the bioluminescence based reactions is due to metabolic changes in a bbioluminescence bacteria or a combination of a luciferase and luciferin; and b) a detector for measuring the emissions.

In yet another aspect, the present invention relates to a method of metal-enhanced bioluminescence sensing, comprising:

a) applying a multiplicity of metallic particles or a metallic material to a substrate used in a detection system;

b) positioning an organism or tissue comprising a bioluminescence generating system near the metallic surface, wherein the bioluminescence generating system generates an electromagnetic energy signal thereby transferring the energy to the metallic surface plasmons; and c) detecting and measuring the bioluminescence signal alone or in combination with emissions from the surface plasmons.

The surface plasmon-coupled bioluminescence signal may include unpolarized, p-polarized and/or s-polarized signals.

Preferably, the metallic material takes the form of metallic particles, such as, nanostructures, islands, colloids; porous matrix; a semi-continuous metallic surface; or metallic particles impregnated with a glass or polymeric surface. Further the metallic material may be formed into a patterned shape. Preferably, the patterned shape includes geometric shapes having at least one apex, such as, a triangle, square, rectangle, trapezoid, polygon, parabola, elliptical, a sector of a circle, oblong and/or combinations thereof, wherein the numerous apexes are adjacent to each other, thereby creating a reactive zone therebetween. The reactive zone therebetween may further be prepared for placement of the immobilized capture molecule complementary to a detector molecule, chemicals for reacting with other chemicals, or biomolecules for reacting with other biomolecules. The reactive zone may have a diameter or distance between the adjacent and/or opposing apexes ranging from about 0.01 mm to 5 mm, and more preferably from about 2 mm to 3 mm. Further, the reactive zone can be positioned on assay system with multiple wells wherein the reactive zone is within the wells and exposure to microwave energy enhances the reactions therein.

The metallic material may include any form of metals such as silver, gold, platinum, zinc, aluminum, indium, palladium, rhodium iron, nickel and copper, and more preferably the metallic material is silver. The substrate may include, glass, quartz, cellulose and/or a polymeric material.

A still further aspect of the present invention relates to the use of low power microwave energy directed at the detection system comprising at least metallic particles for heating of the metallic and/or chemical components therein to enhance the detection system and increase the speed of chemical reactions therein.

Thus, another aspect of the present invention relates to a method for increasing and enhancing bioluminescence signals, the method comprising;

a) applying a multiplicity of metallic particles or metallic material to a substrate or within such substrate used in a detection system;

b) introducing a solution containing at least one biological tissue or organism for disposing near the metallic surface, wherein the biological tissue or organism comprises a bioluminescent substrate;

c) reacting the bioluminescent substrate with a luciferase to induce a chemically electronically excited state thereby producing light and generating metallic surface plasmons; and d) detecting the enhanced bioluminescence signal.

Yet another aspect of the present invention relates to an assay kit, wherein the assay kit comprises i. a substrate surface comprising a metalized surface;

ii. a connector component for attachment to the metalized surface having an affinity for a target component to be determined;

iii. a detector molecule having an affinity for the target component, wherein the detector molecule comprises a first component of a bioluminescence generating system;

iv. a second component of the bioluminescence generating system that chemically reacts with the first component of the bioluminescence generating system to generate a chemically induced electronically exited state.

The bioluminescence generating system may be selected from the group consisting of those isolated from the ctenophores, coelenterases, mollusca, fish, ostracods, insects, bacteria, a crustacea, annelids, and earthworms. The luciferase may be selected from the group consisting of *Aequorea, Vargula, Renilla, Obelin, Porichthys, Odontosyllis, Aristostomias, Pachystomias*, firefly, and bacterial systems.

A still further aspect of the invention relates to a bioassay for measuring concentration of receptor-ligand binding in a test sample, the method comprising:

a) preparing metallic structures immobilized on a surface wherein the metallic structures have positioned thereon a receptor molecule having affinity for a ligand of interest;

b) contacting the receptor molecule with the test sample suspected of comprising the ligand of interest, wherein the ligand of interest will bind to the receptor molecule to form a receptor-ligand complex;

c) contacting the receptor-ligand complex with a detector molecule having affinity for the ligand to form a receptor-ligand-detector complex, wherein the detector molecule comprises a bioluminescence generating system, wherein the a bioluminescence generating system causes the emission of light energy that is transferred and excited metallic surface plasmons; and d) measuring the intensity of radiation emitted from excited metallic surface plasmons and/or test sample.

Preferably, the bioluminescence generating system comprises a first component and a second component that will chemically react with the first component to induce a chemically electronically excited state.

Other features and advantages of the invention will be apparent from the following detailed description, drawings and claims.

A1. Hamamatsu HC135-01 PMT Sensor Module. A2. PMT fixation ring A3. Manual shutter (71430, Oriel). A4. Fiber holder that prevents the movement of the fiber inside the photon counting unit. A5. Fiber optic. A6. Wire connecting PMT to computer. A7. Electricity cable. B. The outside handle of manual shutter that enables light access to the PMT. E. Computer. D. Door. C. Bacteria holding unit. C1. Fiber optic. C2. Fiber optic holder. C3. Fiber optic core without jacket. C4. Well with bacteria. C5. Glass slide. C6. Glass slide covering (silver, silver +SiO2, etc.). (Bottom) Photograph of the glass and glass+2.5 min covered silver wells.

Figure 1:
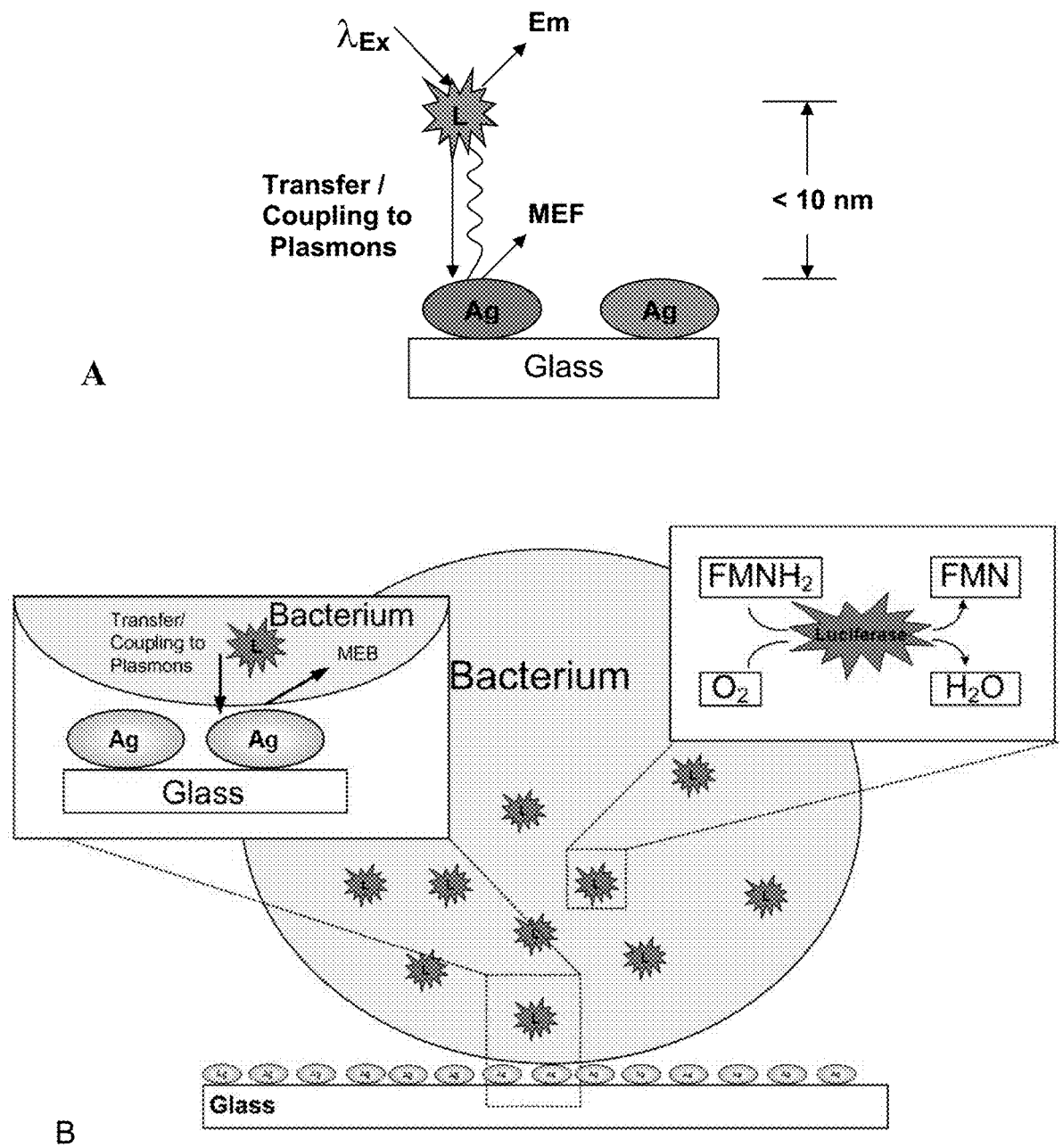
FIG. 1 shows the current interpretation of the mechanism of MEF (Top), and for Metal-Enhanced Bioluminescence, MEB (Bottom).
Figure 2:
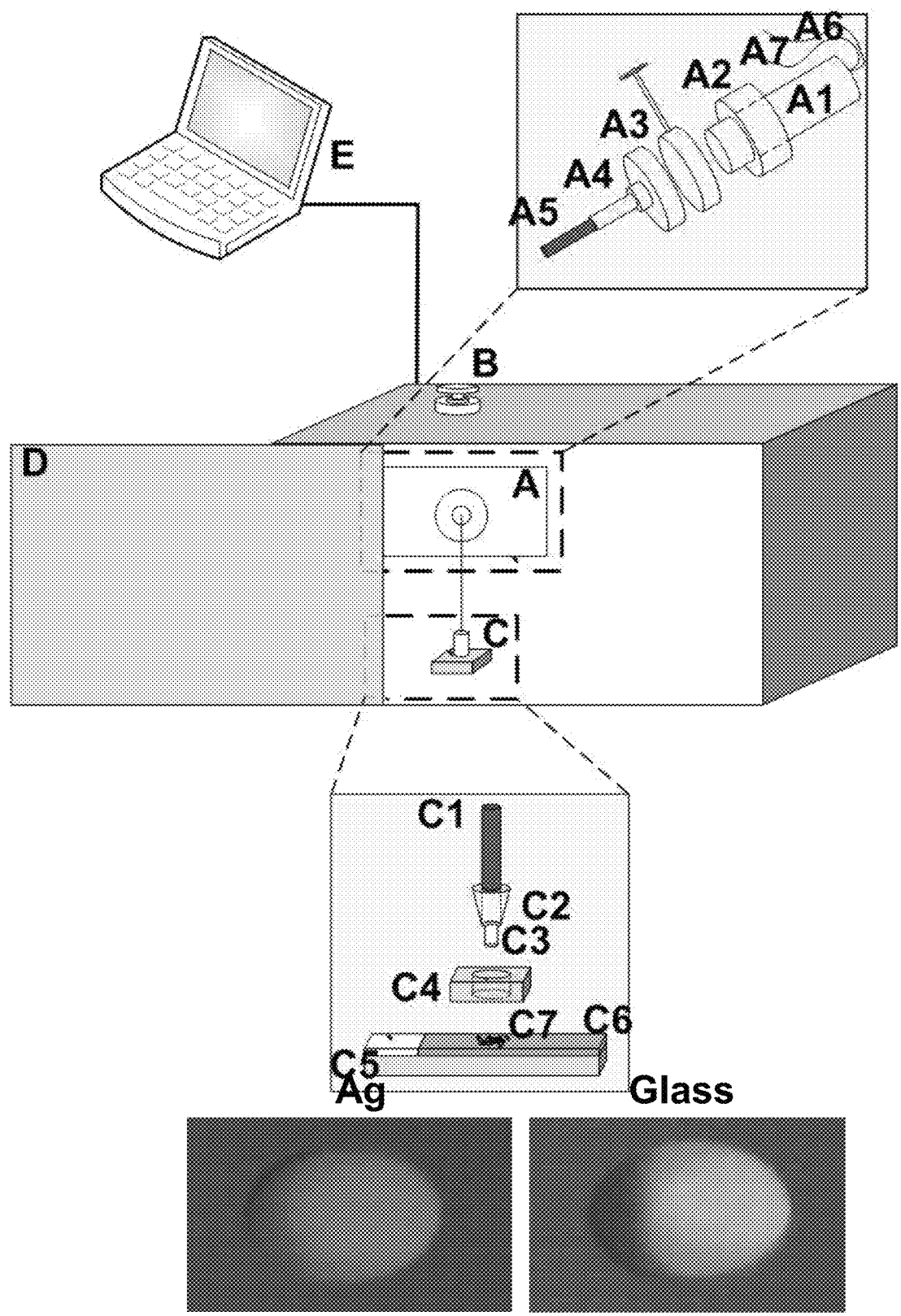
FIG. 2. (Top) Descriptive scheme of the setup for kinetic monitoring of bacterial bioluminescence and Metal-Enhanced Bioluminescence (MEB). A. Photon counting unit.
Figure 3:
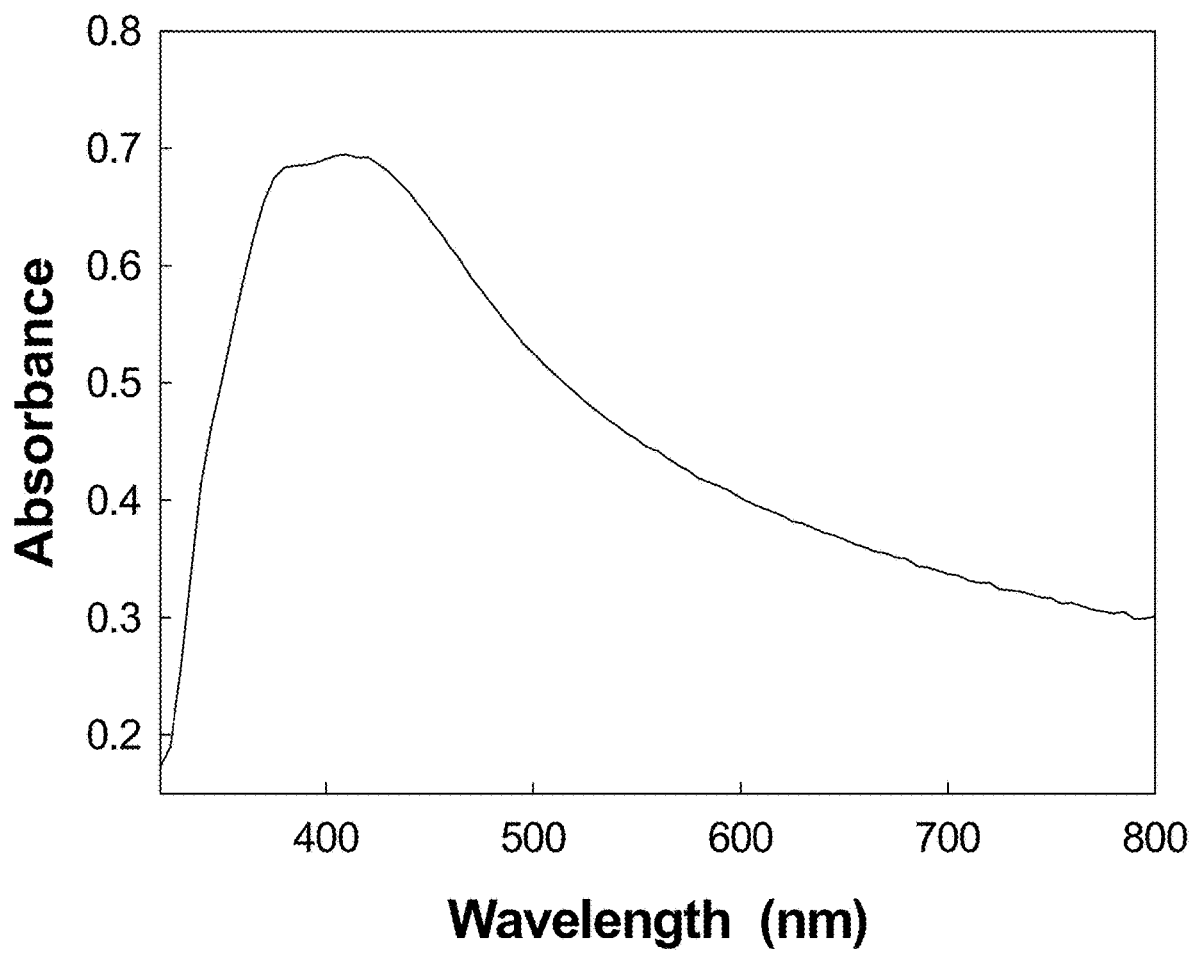
Figure 3:
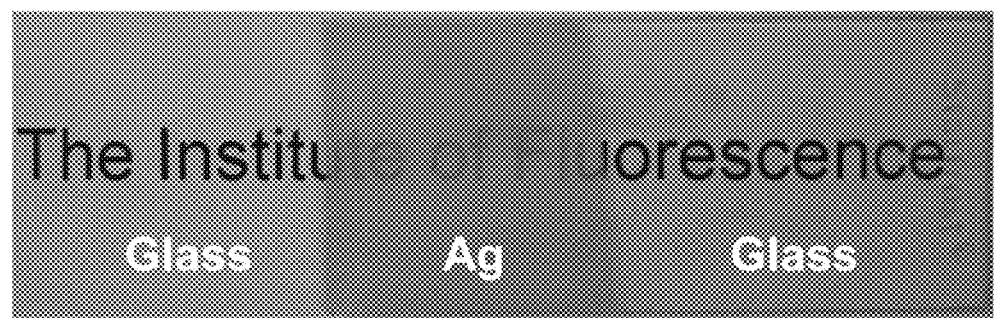

FIG. 3. (Top) Absorption spectrum of silver island films (SiFs). (Bottom) Photograph showing the semi-transparent nature of SiFs (2.5 minute deposition time).

Figure 4:
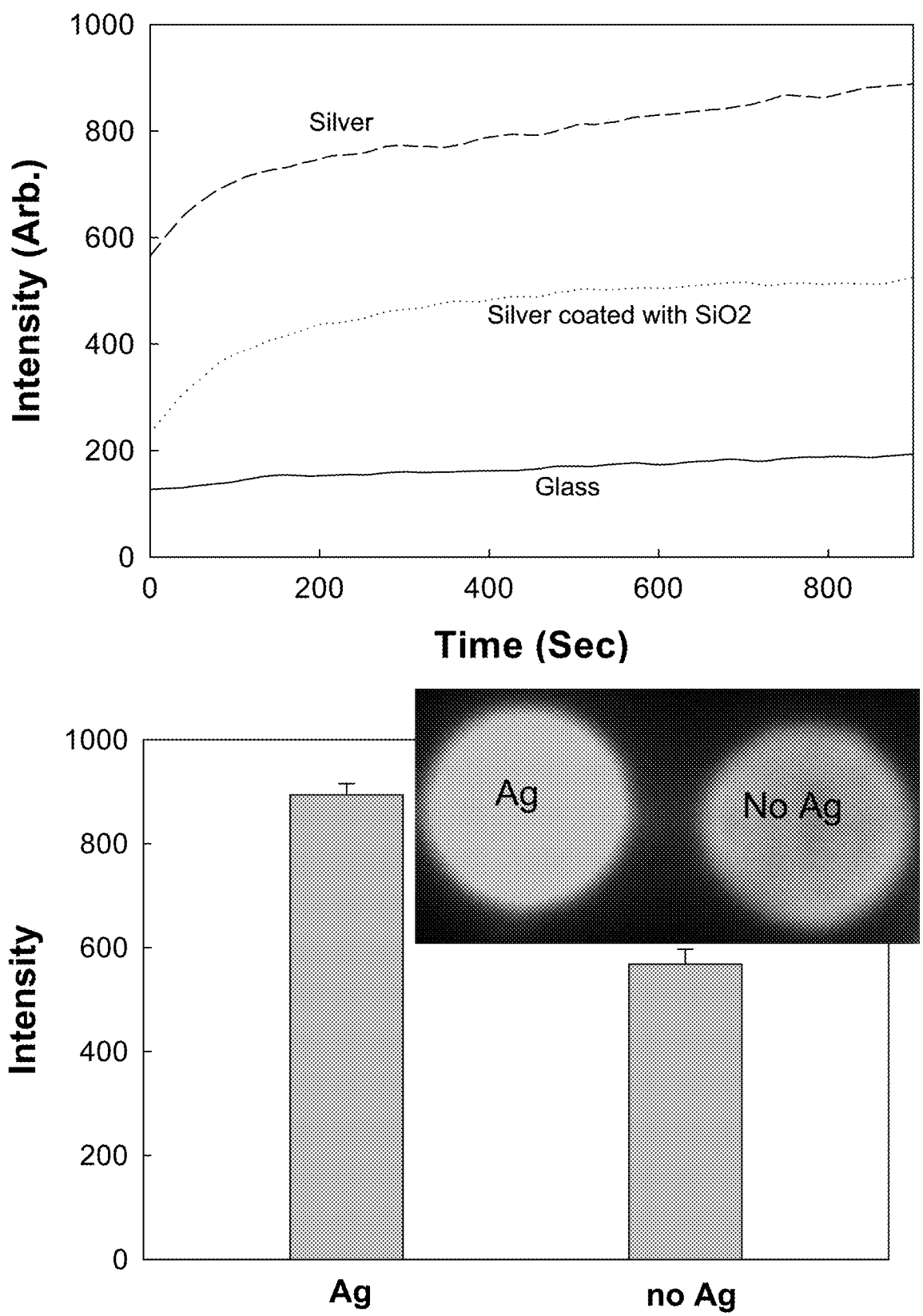

FIG. 4. (Top) Bioluminescent bacteria emission intensity from silvered, silvered glass coated with $SiO_2$ and glass wells as a function of time. (Bottom) Light intensity of bioluminescent bacteria on silver coated glass in comparison to non-coated glass. (Bottom-insert) The intensity of light is much higher in silver coated wells.

DETAILED DESCRIPTION OF THE INVENTION

Bioluminescence is "cold" light produced by a chemical reaction within a living organism. Unlike fluorescence, bioluminescence does not require energy from another source of light to create illumination. As a result, bioluminescence has a much greater range of uses than fluorescence. Bioluminescence research is being conducted for use in numerous diverse fields. For example the use of bioluminescent bacteria may be used to follow the progression of infection in mice. This process could reduce the number of mice used and killed for research, since the development of the disease can be traced while the animal is alive. Specifically, bioluminescent genes (Lux operon) are inserted into salmonella bacteria, causing them to glow. Thus the spread of the infection can be monitored and able to judge which antibiotics are most effective by observing the reduction of the bacteria Although the small size of viruses makes gene insertion more difficult, studies have been initiated to attempt to track the progression of the AIDS virus by changing the cells of the animal to glow when a virus invades.

Further, bioluminescence can be used to track the location of cells altered with gene therapy (including genes that express a Lux operon) to determine if the cells are producing the proper proteins after modification.

By using firefly luciferin, biologists can ascertain the amounts of Adenine Tri-Phosphate (ATP) in plant, animal and bacterial cells. ATP acts as stored energy for these cells and is directly related to the quantity of cells present. In one application of the present invention, the use of ATP can track the incidence and amounts of bacteria present in blood or urine samples. Jellyfish aequorin uses calcium instead of ATP for bioluminescence so this aequorin is used in a similar way to determine the amounts of calcium present.

Still further, bioluminescent organisms can determine the presence or toxicity of certain compounds because of the reaction of the bacteria to the compound. For example, noxious substances can reduce the glow by killing the bacteria. In the alternative, some compounds such as mercury can drive the transcription of bacterial luciferase. Thus such bacteria can be used as biosensor for the detection of mercury in soils and associated environments.

Thus, the present method of enhanced detection can and will improve the sensitivity of such uses.

As used herein, bioluminescence substrate refers to the compound that is oxidized in the presence of a luciferase, and any necessary activators, and generates light. These substrates are referred to as luciferins, which are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, Cypridina [also known as Vargula] luciferin [coelenterazine], bacterial luciferin, as well as synthetic analogs of these substrates or other compounds that are oxidized in the presence of a luciferase in a reaction the produces bioluminescence.

Luciferases refer to any compound that, in the presence of any necessary activators, catalyze the oxidation of a bioluminescence substrate [luciferin] in the presence of molecular oxygen, whether free or bound, from a lower energy state to a higher energy state such that the substrate, upon return to the lower energy state, emits light. For purposes herein, luciferase is broadly used to encompass enzymes that act catalytically to generate light by oxidation of a substrate and also photoproteins, such as aequorin, that act, though not strictly catalytically [since such proteins are exhausted in the reaction], in conjunction with a substrate in the presence of oxygen to generate light. These luciferases, including photoproteins, such as aequorin, are herein also included among the luciferases. These reagents include the naturally-occurring luciferases [including photoproteins], proteins produced by recombinant DNA, and mutated or modified variants thereof that retain the ability to generate light in the presence of an appropriate substrate, co-factors and activators or any other such protein that acts as a catalyst to oxidize a substrate, whereby light is produced.

The luciferases may be obtained commercially, isolated from natural sources, expressed in host cells using DNA encoding the luciferase, or obtained in any manner known to those of skill in the art. For purposes herein, crude extracts obtained by grinding up selected source organisms may suffice. Since large quantities of the luciferase may be desired, isolation of the luciferase from host cells is preferred. DNA for such purposes is widely available as are modified forms thereof.

Examples of luciferases include, but are not limited to, those isolated from the ctenophores Mnemiopsis (Mnemiopsin) and Beroe ovata (berovin), those isolated from the coelenterates Aequorea (aequorin), Obelia (obelin), Pelagia, the Renilla luciferase, the luciferases isolated from the mollusca Pholas (pholasin), the luciferases isolated from the Aristostomias and Porichthys fish and from the ostracods, such as Cypridina (also referred to as Vargula).

The bioluminescence generating systems also require additional components discussed herein and known to those of skill in the art. All bioluminescent reactions require molecular oxygen in the form of dissolved or bound oxygen. Thus, molecular oxygen, dissolved in water or in air or bound to a photoprotein, is the activator for bioluminescence reactions. Depending upon the form of the components, other activators include, but are not limited to, ATP [for firefly luciferase], flavin reductase [bacterial systems] for regenerating $FMNH_2$ from FMN, and $Ca^{2+}$ or other suitable metal ion [aequorin].

As used herein, capable of conversion into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide ($FMNH_2$) by a flavin reductase enzyme. The reduced flavin mononucleotide [substrate] then reacts with oxygen [an activator] and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, bioluminescence system [or bioluminescence generating system] refers to the set of reagents required for a bioluminescence-producing reaction. Thus, the particular luciferase, luciferin and other substrates, solvents and other reagents that may be required to complete a bioluminescent reaction form a bioluminescence system. Therefore, a bioluminescence system (or equivalently a bioluminescence generating system) refers to any set of reagents that, under appropriate reaction conditions, yield bioluminescence. The terminology may further include the cloning and expression of the lux genes from different luminescent bacteria including marine and terrestrial species. All lux operons have a common gene organization of luxCDAB(F)E, with luxAB coding for luciferase and luxCDE coding for the fatty acid reductase complex responsible for synthesizing fatty aldehydes for the luminescence reaction. The lux genes can be transferred into a variety of different organisms to generate new luminescent species. The ability to express the lux genes in a variety of prokaryotic and eukaryotic organisms and the ease and sensitivity of the luminescence assay demonstrate the considerable potential of the widespread application of the lux genes as reporters of gene expression and metabolic function.

It is understood that a bioluminescence generating system may be isolated from natural sources, or may be produced synthetically. In addition, for uses herein, the components need only be sufficiently pure so that mixture thereof, under appropriate reaction conditions, produces a glow. Thus it has been found, in some embodiments, a crude extract or merely grinding up the organism may be adequate.

Most of the systems provided herein will generate light when the luciferase and luciferin are mixed and exposed to air or water. The systems that use photoproteins that have bound oxygen, such as aequorin, however, will require exposure to Ca' [or other suitable metal ion], which can be provided in the form of an aqueous composition of a calcium salt.

Virtually any bioluminescence generating system known to those of skill in the art will be amenable to use in the apparatus, systems, combinations and methods provided herein. Factors for consideration in selecting a bioluminescence generating system, include, but are not limited to: the desired assay and biological fluid used in combination with the bioluminescence; the medium in which the reaction is run and appropriate reaction conditions; stability of the components, such as temperature or pH sensitivity; shelf life of the components; sustainability of the light emission, whether constant or intermittent; availability of components; desired light intensity; and other such factors.

Appropriate reaction conditions refer to the conditions necessary for a bioluminescence reaction to occur, such as pH, salt concentrations and temperature.

As used herein, ATP, AMP, NAD+ and NADH refer to adenosine triphosphate, adenosine monophosphate, nicotinamide adenine dinucleotide (oxidized form) and nicotinamide adenine dinucleotide (reduced form), respectively.

As used herein, production by recombinant means by using recombinant DNA methods means the use of the well known methods of molecular biology for expressing proteins encoded by cloned DNA.

As used herein, "receptor-ligand" refers to any naturally occurring or unnaturally occurring binding couple wherein the components have affinity for each other. For example, the binding couple may include an antibody/antigen complex, viral coat ligand/protein cell receptor or any combination of probe and binding partner. The term "receptor" refers to a chemical group, molecule, biological agent, naturally occurring or synthetic that has an affinity for a specific chemical group, molecule, virus, probe or any biological agent target in a sample. The choice of a receptor-ligand for use in the present invention will be determined by nature of the disease, condition, or infection to be assayed.

Surprisingly, the present invention shows that chemically induced electronic excited states (bioluminescence species) also couple to surface plasmons, producing emission intensities from about 5 to about 1000 fold greater, as compared to a control sample containing no surface silver nanostructures. This approach is of significance for optically amplifying bioluminescence based clinical assays, potentially increasing analyte/biospecies detectability.

Surface plasmons are collective oscillations of free electrons at metallic surfaces. When a metallic article or surface is exposed to an electromagnetic wave, the electrons in the metal (plasmons) oscillate at the same frequency as the incident wave. Subsequently, the oscillating electrons radiate electromagnetic radiation with the same frequency as the oscillating electrons. It is this re-radiation of light at the same incident wavelength that is often referred to as plasmon emission.

The present invention provides enhanced emissions using metalized nanostructures, islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 50 nm apart.

Metal island particles may be prepared in clean beakers by reduction of metal ions using various reducing agents. For example, sodium hydroxide is added to a rapidly stirred silver nitrate solution forming a brown precipitate. Ammonium hydroxide is added to re-dissolve the precipitate. The solution is cooled and dried quartz slides are added to the beaker, followed by glucose. After stirring for 2 minutes, the mixture is warmed to 30° C. After 10-15 minutes, the mixture turns yellow-green and becomes cloudy. A thin film of silver particles has formed on the slides as can be seen from their brown green color. The slides are rinsed with pure water prior to use. Alternative procedures for preparing metal particles are also available.

Colloids can be prepared as suspensions by citrate reduction metals. Preferred metals are silver and gold. The size of the colloids and their homogeneity can be determined by the extensive publications on the optical properties of metal particles available and the effects of interface chemistry on the optical property of colloids.

Metal particles can be bound to a surface by placing functional chemical groups such as cyanide (CN), amine ($NH_2$) or thiol (SH), on a glass or polymer substrate. Metal colloids are known to spontaneously bind to such surfaces with high affinity.

Metal-bioluminescence species distances may be achieved by using polymer films. Examples of the polymer include, but not limited to, polyvinyl alcohol (PVA). Absorbance measurements and ellipsometry may be used to determine polymer film thickness. One type of polymer films is spin coated polymer films. The technology of spin coated polymer spacer films readily allows films to be coated onto a variety of surfaces, with varied thickness from >0.1 um. The coating can be performed on a spin coater, which allows uniform surface thickness by varying polymer concentration (viscosity) and spin speed. For example, Model P6700 spin coater (Specialty Coating Systems Inc.) allows uniform surface thickness by varying polymer concentration (viscosity) and spin speed.

Metallic colloids (or various other non-spherical shapes/particles) may also be incorporated into organic polymers, covalently or non-covalently, to form polymeric matrices, wherein the distance from diffusing species affords an increase in radiative decay rate and thus, an increase in quantum yield. Such polymeric matrices are ideal for sensing/flowing sensing applications of low concentration species.

The present invention provides for metalized islands of elliptical, spherical, triangular or rod-like forms. In exemplary cases, the elliptical islands have aspect ratios of 3/2, and the spherical colloids have diameters of 20-60 nm. However, the invention is not limited to any particular geometry. Using known coating techniques, the placement of metallic islands could be controlled precisely, as close as 10 to 50 nm apart.

The metallic material may be in the form of a porous three dimensional matrix. The three dimensional matrix may be a nano-porous three dimensional matrix. The metallic material may include metal colloid particles and/or metal-silica composite particles. The metallic material may comprise agglomerated metal particles and/or binary linked particles or metal particles in a polymer matrix. The three dimensional matrix may be formed from controlled pore glasses or using matrices assembled from the aggregation of silver-silica composites themselves. The matrices may be metallic nanoporous matrix, through which species will flow and be both detected and counted more efficiently.

The emission from the bioluminescence reaction may be observed at distances from about 5 nm to about 200 nm to metal surfaces. Preferable distances are about 5 nm to about 50 nm, and more preferably, 10 nm to about 30 nm to metal surfaces. At this scale, there are few phenomena that provide opportunities for new levels of sensing, manipulation, and control. In addition, devices at this scale may lead to dramatically enhanced performance, sensitivity, and reliability with dramatically decreased size, weight, and therefore cost.

The present invention further comprises a detection device for detecting emissions including, but not limited to visual inspection, digital (CCD) cameras, video cameras, photographic film, or the use of current instrumentation such as laser scanning devices, luminometers, photodiodes, fiber optics, quantum counters, plate readers, scanning microscopes, confocal microscopes, capillary electrophoresis detectors, or other light detector capable of detecting the presence, location, intensity, excitation and emission spectra.

The application of low level microwave energy for heating of the sample may be used to speed up any biological/biochemical kinetics within the system. Notably, low level microwaves do not destroy or denature proteins, DNA, or RNA, but instead heat the sample sufficiently to provide for accelerated kinetics such as binding, hybridization or chemical interaction.

Microwaves (about 0.3 to about 300 GHz) lie between the infrared and radio frequency electromagnetic radiations. It is widely thought that microwaves accelerate chemical and biochemical reactions by the heating effect, where the heating essentially follows the principle of microwave dielectric loss. Polar molecules absorb microwave radiation through dipole rotations and hence are heated, where as non-polar molecules do not absorb due to lower dielectric constants are thus not heated. The polar molecules align themselves with the external applied field. In the conventional microwave oven cavity employed in this work, the radiation frequency (2450 MHz) changes sign $2.45\times10^9$ times per second. Heating occurs due to the tortional effect as the polar molecules rotate back and forth, continually realigning with the changing field, the molecular rotations being slower than the changing electric field. The dielectric constant, the ability of a molecule to be polarized by an electric field, indicates the capacity of the medium to be microwave heated. Thus, solvents such as water, methanol and dimethyl formamide are easily heated, where as microwaves are effectively transparent to hexane, toluene and diethylether.

In the present invention, microwave radiation may be provided by an electromagnetic source having a frequency in a range between 0.3 and 10 GHz, more preferably from about 1 GHz and 5 GHz, and more preferably from 2 GZ to 3 GZ, and a power level in a range between about 10 mwatts and 700 watts, preferably from 30 mwatts to about 500 watts, and more preferably from about 50 watts to 300 watts. Any source, known to one skilled in the art may be used, such as a laser having the capacity to emit energy in the microwave range. The microwave radiation may be emitted continuously or intermittently (pulsed), as desired.

In the alternative, microwave energy can be supplied through a hollow wave guide for conveying microwave energy from a suitable magnetron. The microwave energy is preferably adjusted to cause an increase of heat within the metallic material without causing damage to any biological materials in the assay system.

There are many important assays that can directly benefit from enhanced signal intensities and quicker kinetics. Such increase in kinetics can be achieved by using any device capable of generating and transmitting acoustic energy through any medium to transit ultrasonic atomizing energy. The ultrasonic emitting device can be placed in either the interior of a vessel or positioned adjacent thereto for transmitting energy into the vessel. The device may include components for the traditional electromagnetic stimulation of piezoelectric transducers, (man-made or naturally occurring), purely mechanical devices (such as high frequency air whistles or microphones), and laser devices. Individual components for acoustic energy systems are commercially available from a wide variety of manufacturers, which can be configured to particular applications and frequency ranges. (See Thomas Directory of American Manufacturers, Photonics Buyer's Guide, 1996, Microwave and RF, and Electronic Engineer's Master Catalogue).

Any oscillator or signal generator that produces a signal with predetermined characteristics such as frequency, mode, pulse duration, shape, and repetition rate may be used to generate acoustic frequencies for applying to the system of the present invention. Various oscillators or signal generators can be commercially purchased from a wide variety of manufacturers and in a variety of designs configured to particular applications and frequencies. Applicable transducers will include types that produce an acoustic wave within a range of frequencies (broadband) or for one specific frequency (narrowband) for frequencies ranging from hertz to gigahertz.

The acoustic delivery system will be variable depending on the application. For example, acoustic energy waves can be transmitted into liquid or solid source material either by direct contact of the source material with a transducer, or by coupling of transmission of the acoustic wave through another medium, which is itself in direct contact with the source material. If the source material is a liquid, a transducer can be placed in the liquid source material, or the walls of the vaporization vessel can be fabricated of a material that acts as a transducer thereby placing the liquid source material in direct contact with the transducer. Additionally, an acoustic energy emitting device may be positioned on the exterior of a system container for transmitting the appropriate energy. If the source material is a solid, a transducer can be placed in direct contact with it or the solid source material can be placed in a gas or liquid that is used as a coupling agent.

In the preferred acoustic frequencies any system that generates acoustic energy may be utilized. Preferably, the output of the ultrasonic generator is of a sufficient frequency to provide a movement flow within the system vessel to move molecules to the source of binding or reaction site without causing a large increase of heat in the system. For example, using the power output of 0.5 to 50 W at a frequency of 10 to 200 kHz, and more preferably from about 20 to 60 kHz and most preferably at about 40 kHz.

To obtain the maximum transfer of acoustical energy from one medium to another, the characteristic acoustical impedance of each medium is preferably as nearly equal to the other as possible. The matching medium is sandwiched between the other two and should be the appropriate thickness relative to the wavelength of the sound transmitted, and its acoustical impedance R should be nearly equal to ($R_1$:$R_2$). Any impedance matching device that is commercially available can be utilized in the present invention.

The system may include ultrasonic vessels wherein at least a section of the vessel includes a transducer such as a piezoelectric transducer to generate acoustic vibrations. Such transducers can be located in the bottom of a vessel or in a plate whereon a vessel may be placed. Further such transducers can be placed at different levels on the vessel walls to enhance fluid flow within the vessel.

EXAMPLES

The observation of Metal (Plasmon)-enhanced Bioluminescence is reported herein. Bacteria, which are capable of generating specific Bioluminescence signatures upon metabolic changes (general toxicity) have been studied from both glass and silvered glass microwell bottoms, where the silvered microwells have been modified with surface deposited Silver Island Films (SiFs). The presence of the SiFs plasmon-amplifies the near-field Bioluminescence signatures, <50 nm from the surface, enabling amplified detection of the reporter Bioluminescence indicating sample toxicity. Using our approach a greater than 5-fold enhancement in far-field Bioluminescence occurs, with much greater enhancements in the near-field predicted.

The results described herein show results that are similar to fluorescence, phosphorescence and chemiluminescence based approaches, Metal-Enhanced Bioluminescence can also be used to Plasmon-enhance Bioluminescence signatures, FIG. 1—Bottom, enabling the much more sensitive detection of Bioluminescence with potential multifarious applications in the Biosciences.

SiFs were deposited on glass slides as was described earlier.[18] The bioluminescent *Escherichia coli* strain TV1061" used in this study is sensitive to metabolic changes, such as with cytotoxic substances. This bacterium harbors plasmid-borne fusions specific heat-shock grpE promoter to the iuxCDABE reporter operon.[20] The tested bacteria were induced with a positive control (2% (v/v) ethanol) and after 1.5 hours incubation at 26° C. these were placed on ice, in order to maintain the bacterial concentration, and measured using a field-operable fiber-optic photodetector device,[21] as shown in FIG. 2 top. Effects of three different matrices on bacterial bioluminescence were tested using glass slides, glass slides covered with SiFs and glass slides with $SiO_2$ covered SiFs. The differences in the light intensity were measured with a Hamamatsu HC135-01 PMT Sensor Module and photographed in real time with a CCD camera (Retiga-SRV fast 1394, QImaging, Canada).

FIG. 3—Top shows the plasmon absorption spectra of SiFs, where the surface plasmon absorption is well-known to be characteristic of both the shape, size and type of metal of the nanoparticles immobilized on the glass surface.[22] In this case, the shape of the plasmon absorption band was similar to the shapes typically observed on the glass substrates, with a peak near 425 nm.[2,23] The SiFs are non-continuous semi-transparent silver nano-deposits, as shown in FIG. 3—Bottom.

FIG. 4 visually demonstrates the benefits of the Metal-enhanced Bioluminescence. Bioluminescent emission observed from bacteria located on SiFs was ≈1.5 fold higher in comparison to non-silvered coated glass (FIG. 4—Bottom). The color photograph inserts provide visual evidence for enhanced bacterial luminescence from the silver film. This phenomenon is due to the enhancement of bioluminescence emission by the silver nanoparticles (that is, Metal-enhanced Bioluminescence): excited bacterial luciferase molecules that are located in close-proximity to the silvered surface transfer their energy to the silver nanoparticles, where the energy is coupled efficiently and the emission from the bacteria—silver 'system' becomes greater than the bioluminescence signal from bacteria alone, i.e. it is plasmon amplified. Kinetic measurements (FIG. 4—Top) support these findings. While in this case, there is up to 5 fold difference in the light intensity between bacteria placed on the silvered and non-silvered coated glass surfaces. Metal-enhanced Bioluminescence demonstrates a clear distance dependence of excited-state coupling: as the distance between silver islands and bacteria increases (such as by adding an inert $SiO_2$ layer), the far-field total light enhancement decreases (FIG. 4—Top). Whole cell optic biosensors have been already proposed for use in many environmental applications.[26,27] Thus, increasing the light intensity will invariably increase the sensitivity and eventually attractiveness of these constructs in the future.

In yet another embodiment, an oxide layer is positioned on the metallic structures to protect the bacteria species from contact with the metallic particles. The oxide layer may be formed from a deposition technique, such as vapor deposition. The oxide layer coating may include at least one metal selected from the group consisting of Al, Ti, Fe, Cu, Zn, Y, Zr, Nb, Mo, In, Si, Sn, Sb, Ta, W, Pb, Bi and Ce and having a valence of from 2 to 6. The form of the oxide of such a metal may, for example, be $Al_2O_3$, $SiO_2$, $TiO_2$, $Fe_2O_3$, CuO, ZnO, $Y_2O_3$, $ZrO_2$, $Nb_2O_5$, $MoO_3$, $In_2O_3$, $SnO_2$, $Sb_2O_5$, $Ta_2O_5$, $WO_3$, PbO or $Bi_2O_3$. These metal oxides may be used alone or in combination with other types of coatings.

Preferably, the oxide is a silicon oxide, more preferably, $SiO_2$. The vapor deposition of $SiO_2$ is a well established technique for the controlled deposition of a variety of substrates. For example, an Edwards Vapor deposition module allows the deposition of an inert coating of $SiO_2$.

In conclusion, the observation of Metal-Enhanced Bioluminescence (MEB) bioluminescence signatures generated in close-proximity to the metallic surfaces demonstrates enhanced emission as compared to a non-silvered coated glass control sample containing the same number of bacteria. The bacteria are unperturbed by the silvered surface and show a greater than 5-fold enhancement in the far-field bioluminescence detected as compared to the control sample. Interestingly, this enhancement originates from less than 10 nm of bacterial sample, i.e. MEB interaction coupling distance, suggesting that the near-field enhancements are considerably larger.

REFERENCES

The contents of the all references cited herein are incorporated by reference herein for all purposes.
1. K. Aslan, I. Gryczynski, J. Malicka, E. Matveeva, J. R. Lakowicz, and C. D. Geddes, *Curr Opin Biotechnol* 16,55-62 (2005).
2. K. Aslan, S. N. Malyn, and C. D. Geddes, *Analyst* 132, 1112-1121 (2007).
3. J. R. Lakowicz, C. D. Geddes, I. Gryczynski, J. Malicka, Z. Gryczynski, K. Aslan, J. Lukomska, E. Matveeva, J. Zhang, R. Badugu, and J. Huang, *J Fluoresc* 14, 425-441 (2004).
4. Y. Zhang, K. Aslan, S. N. Malyn, and C. D. Geddes, *Chemical Physics Letters* 427 432-437 (2006).
5. Y. Zhang, K. Aslan, M. J. Previte, S. N. Malyn, and C. D. Geddes, *J Phys Chem B* 110, 25108-25114 (2006).
6. M. H Chowdhury, K. Aslan, S. N. Malyn, J. R. Lakowicz, and C. D. Geddes, *Applied Physics Letters* 882006).
7. K. Aslan and C. D. Geddes, *Analyst* 133, 1469-1480 (2008).
8. K. Aslan and C. D. Geddes, *Plasmonics* 3, 89-101 (2008).
9. K. Aslan, S. N. Malyn, and C. D. Geddes, *Chem Phys Lett* 453, 222-228 (2008).
10. K. Aslan, M. Wu, J. R. Lakowicz, and C. D. Geddes, *J Am Chem Soc* 129, 1524-1525 (2007).
11. K. Aslan, M. J. Previte, Y. Zhang, T. Gallagher, L. Baillie, and C. D. Geddes, *Anal Chem* 80, 4125-4132 (2008).
12. T. Troy, D. Jekic-McMullen, L. Sambucetti, and B. Rice, *Mol Imaging* 3, 9-23 (2004).
13. S. K. Nordeen, *Biotechniques* 6, 454-458 (1988).
14. B. Polyak, S. Geresh, and R. S. Marks, *Biomacromolecules* 5, 389-396 (2004).
15. E. Eltzov, D. Zeevi, A. Kushmaro, and R. S. Marks, *Sensors and Actuators B: Chemical* 129, 685-692 (2008).
16. S. Belkin, D. R. Smulski, A. C. Vollmer, T. K. Van Dyk, and R. A. LaRossa, *Appl Environ Microbiol* 62, 2252-2256 (1996).
17. R. Pedahzur, B. Polyak, R. S. Marks, and S. Belkin, *J Appl Toxicol* 24, 343-348 (2004).
18. K. Aslan, Z. Leonenko, J. R. Lakowicz, and C. D. Geddes, *J Fluoresc* 15, 643-654 (2005).
19. T. K. Van Dyk, W. R. Majarian, K. B. Konstantinov, R. M. Young, P. S. Dhurjati, and R. A. LaRossa, *Appl Environ Microbiol* 60, 1414-1420 (1994).
20. E. A. Meighen, *Faseb J* 7, 1016-1022 (1993).
21. B. Polyak, E. Bassis, A. Novodvorets, S. Belkin, and R. S. Marks, *Wat Sci Technol* 42, 305-311 (2000).
22. S. Link and M. A. El-Sayed, *The Journal of Physical Chemistry B* 103, 8410-8426 (1999).
23. K. Aslan, J. R. Lakowicz, and C. D. Geddes, *Analytical Chemistry* 77, 2007-2014 (2005).
24. A. Wokaun, H. P. Lutz, A. P. King, U. P. Wild, and R. R. Ernst, *Journal of Chemical Physics* 79, 509-514 (1983).
25 P. J. Tarcha, J. DeSaja-Gonzalez, S. Rodriquez-Llorente, and R. Aroca, *Applied Spectroscopy* 53, 43-48 (1999).
26. R. S. Marks, D. C. Cullen, I. Karube, C. R. Lowe, and H. H. Weetall, *Handbook of biosensors and biochips*. (John Wiley & Sons, Ltd., 2007).
27. T. Fine, P. Leskinen, T. Isobe, H. Shiraishi, M. Morita, R. S. Marks, and M. Virta, *Biosensors & Bioelectronics* 21, 2263-2269 (2006).

That which is claimed is:

1. A bioassay for measuring concentration of a ligand of interest in a test sample, the method comprising:
    a) preparing metallic structures immobilized on a substrate surface wherein the metallic structures have positioned thereon a receptor molecule having affinity for the ligand of interest, wherein the substrate surface is glass, quartz, cellulose and/or a polymeric material, wherein the metallic structures are nanostructures, islands, or colloids having a diameter size of from 20 to 60 nm and wherein the metallic structures are positioned 10 to 50 nm apart from one another;
    b) contacting the receptor molecule with the test sample suspected of comprising the ligand of interest, wherein the ligand of interest will bind to the receptor molecule to form a receptor-ligand complex;
    c) contacting the receptor-ligand complex with a detector molecule having affinity for the ligand of interest to form a receptor-ligand-detector complex, wherein the detector molecule comprises a bioluminescence generating system comprising a bioluminescence substrate, wherein the bioluminescence substrate is positioned from about 5 nm to about 50 nm from the metallic structures, and wherein the bioluminescence generating system emits light energy that is transferred to metallic surface plasmons; and
    d) detecting and measuring an intensity of emissions and using the measured intensity to quantify the concentration of the ligand in the test sample,
wherein the emissions detected and measured include radiation from the bioluminescence generating system in combination with plasmonic emissions from the metallic structures, wherein the plasmonic emissions are generated without an external excitation source.

2. The bioassay of claim 1, wherein the bioluminescence generating system comprises a first component and a second component that will chemically react with the first component to induce a chemically electronically excited state.

3. The bioassay of claim 2, wherein the first component is luciferin that is oxidized by the second component luciferase.

4. The bioassay of claim 1, wherein the metallic structures are fabricated of silver, gold, platinum, zinc, aluminum, indium, palladium, rhodium iron, nickel, copper or combinations thereof.

5. The bioassay of claim 1, wherein the bioluminescence generating system includes oxidation of a luciferin by a luciferase or expression of the lux luciferase operon, wherein the luciferase is found in an organism selected from the group consisting of *Mnemiopsis, Beroe ovate, Aequorea, Pelagia, Vargula, Renilla, Pholas, Obelin, Porichthys, Odontosyllis, Aristostomias, Pachystomias,* firefly, and bacterial systems.

6. The bioassay of claim 5, wherein the luciferin is selected from the group consisting of firefly luciferin, *Vargula luciferin, bacterial luciferin*, and synthetic analogs thereof.

7. The bioassay of claim 5, wherein the lux luciferase operon have a common gene organization of luxCDAB(F)E, with luxAB coding for luciferase and luxCDE coding for a fatty acid reductase complex responsible for synthesizing fatty aldehydes for a luminescence reaction.

8. The bioassay of claim 5, wherein the bioluminescence generating system further comprises molecular oxygen.

9. The bioassay of claim 5, wherein the bioluminescence generating system further comprises Adenine Tri-Phosphate (ATP) when the luciferase comprises firefly luciferase, flavin reductase when the luciferase is comprised in a bacterial system, and $Ca^{2+}$ or other suitable metal ion when the luciferase comprises Aequorin.

10. The bioassay of claim 1, wherein the bioluminescence generating system is isolated from natural sources or is produced synthetically.

11. The bioassay of claim 1, wherein the receptor-ligand complex is an antibody/antigen complex or a viral coat ligand/protein cell receptor complex.

12. The bioassay of claim 1, wherein the metallic structures are patterned shapes selected from the group consisting of a triangle, a square, a rectangle, a trapezoid, a polygon, a parabola, a ellipse, a sector of a circle, an oblong, and any combination thereof.

* * * * *